US007736342B2

(12) United States Patent
Abriles et al.

(10) Patent No.: US 7,736,342 B2
(45) Date of Patent: Jun. 15, 2010

(54) ENCLOSED NEEDLE CANNULA DEVICE WITH PROXIMAL END CAP

(75) Inventors: Oscar R. Abriles, Madison, CT (US); Thomas T. Koehler, Simsbury, CT (US)

(73) Assignee: Smiths Medical ASD, Inc., Rockland, MA (US)

(*) Notice: Subject to any disclaimer, the term of this patent is extended or adjusted under 35 U.S.C. 154(b) by 193 days.

(21) Appl. No.: 11/755,200

(22) Filed: May 30, 2007

(65) Prior Publication Data
US 2008/0300543 A1    Dec. 4, 2008

(51) Int. Cl.
*A61M 5/32* (2006.01)
(52) U.S. Cl. .................. 604/192; 604/162
(58) Field of Classification Search ............ 604/162, 604/192–198
See application file for complete search history.

(56) References Cited

U.S. PATENT DOCUMENTS

| | | | |
|---|---|---|---|
| 4,248,246 A | 2/1981 | Ikeda | |
| 4,747,831 A | 5/1988 | Kulli | |
| 4,834,718 A | 5/1989 | McDonald | |
| 4,846,805 A | 7/1989 | Sitar | |
| 4,850,961 A | 7/1989 | Wanderer et al. | |
| 4,938,745 A * | 7/1990 | Sagstetter | 604/263 |
| 4,944,725 A | 7/1990 | McDonald | |
| 4,944,728 A | 7/1990 | Carrell et al. | |
| 5,013,304 A * | 5/1991 | Russell et al. | 604/167.03 |
| 5,032,116 A | 7/1991 | Peterson | |
| 5,382,240 A | 1/1995 | Lam | |
| 5,725,503 A | 3/1998 | Arnett | |
| 5,769,827 A | 6/1998 | DeMichelle et al. | |
| 5,795,339 A | 8/1998 | Erskine | |
| 5,817,058 A | 10/1998 | Shaw | |
| 5,830,190 A | 11/1998 | Howell | |
| 6,090,078 A | 7/2000 | Erskine | |
| 6,221,047 B1 | 4/2001 | Greene et al. | |

(Continued)

FOREIGN PATENT DOCUMENTS

EP    1417983 A    5/2004

(Continued)

OTHER PUBLICATIONS

International Search Report for PCT/US2008/060446 mailed on Jun. 19, 2008 (4 pages).

(Continued)

*Primary Examiner*—Nicholas D Lucchesi
*Assistant Examiner*—Gerald Landry, II
(74) *Attorney, Agent, or Firm*—Wood, Herron & Evans, LLP

(57) ABSTRACT

An enclosed needle catheter insertion device includes a catheter assembly and a need insertion device having a needle guard housing to enclose a needle in a shielded position and a needle support supporting the needle for movement between a ready position, with the tip of the needle exposed, to a shielded position with the needle within the needle guard housing. Movement of the needle support and the needle relative to the needle guard housing is accomplished by manual manipulation of a gripping component external of the needle guard housing. A separate, proximal end cap external of the needle guard housing encloses a proximal portion of the needle guard housing, and is affixed to the needle support.

42 Claims, 9 Drawing Sheets

U.S. PATENT DOCUMENTS

| | | |
|---|---|---|
| 6,436,070 B1 | 8/2002 | Botich et al. |
| 6,582,402 B1 | 6/2003 | Erskine |
| 6,616,631 B2 * | 9/2003 | Takagi et al. ............... 604/110 |
| 6,878,134 B2 | 4/2005 | Rogers et al. |
| 6,986,760 B2 | 1/2006 | Giambattista et al. |
| 7,125,396 B2 | 10/2006 | Leinsing et al. |
| 7,255,685 B2 | 8/2007 | Pressly, Sr. et al. |
| 7,585,287 B2 | 9/2009 | Bresina et al. |
| 2002/0156422 A1 * | 10/2002 | Takagi et al. ............ 604/164.12 |
| 2004/0267204 A1 * | 12/2004 | Brustowicz ............ 604/168.01 |

FOREIGN PATENT DOCUMENTS

| | | |
|---|---|---|
| WO | 9805374 A | 2/1998 |

OTHER PUBLICATIONS

Written Opinion for PCT/US2008/060446 mailed on Jun. 19, 2008 (6 pages).

* cited by examiner

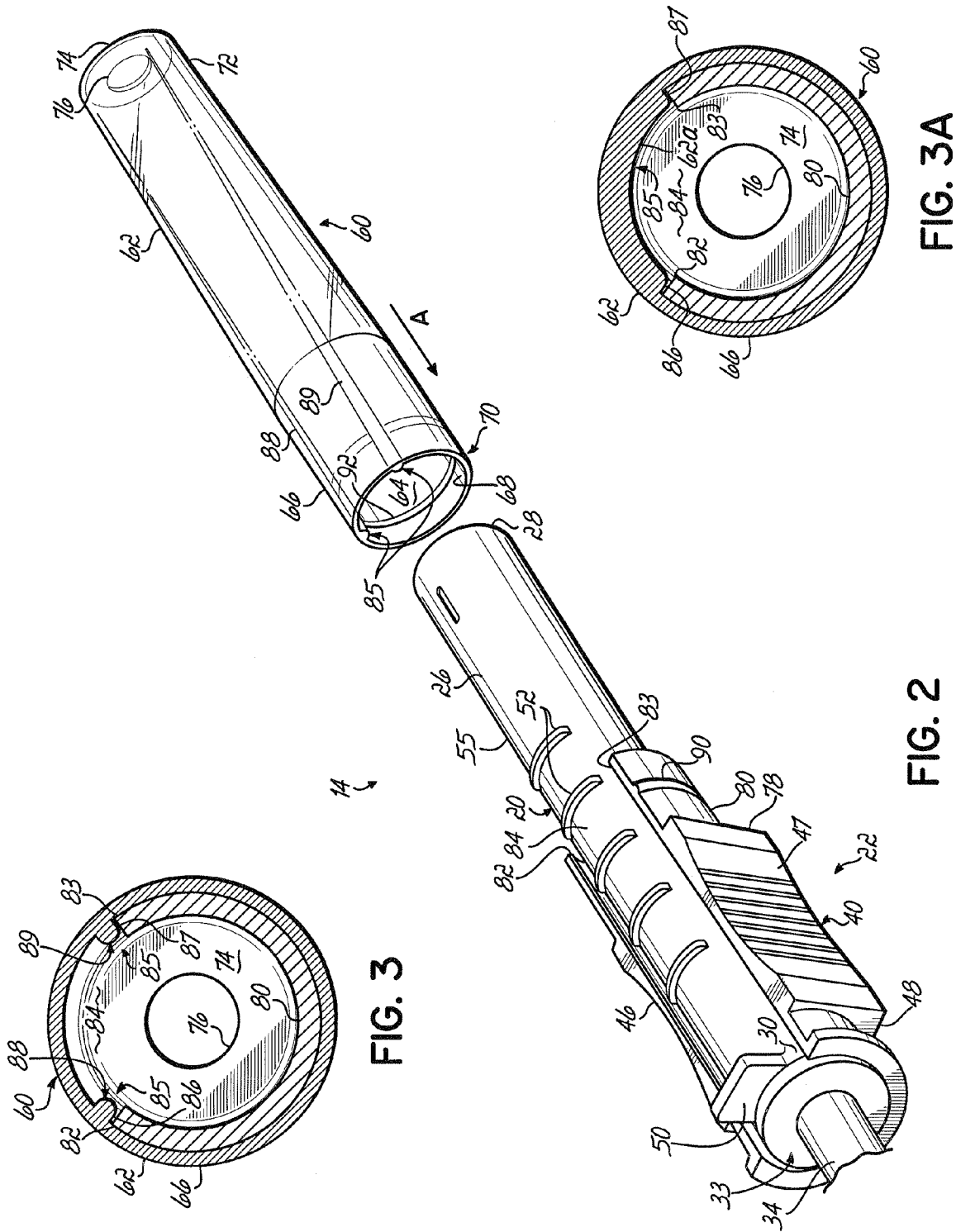

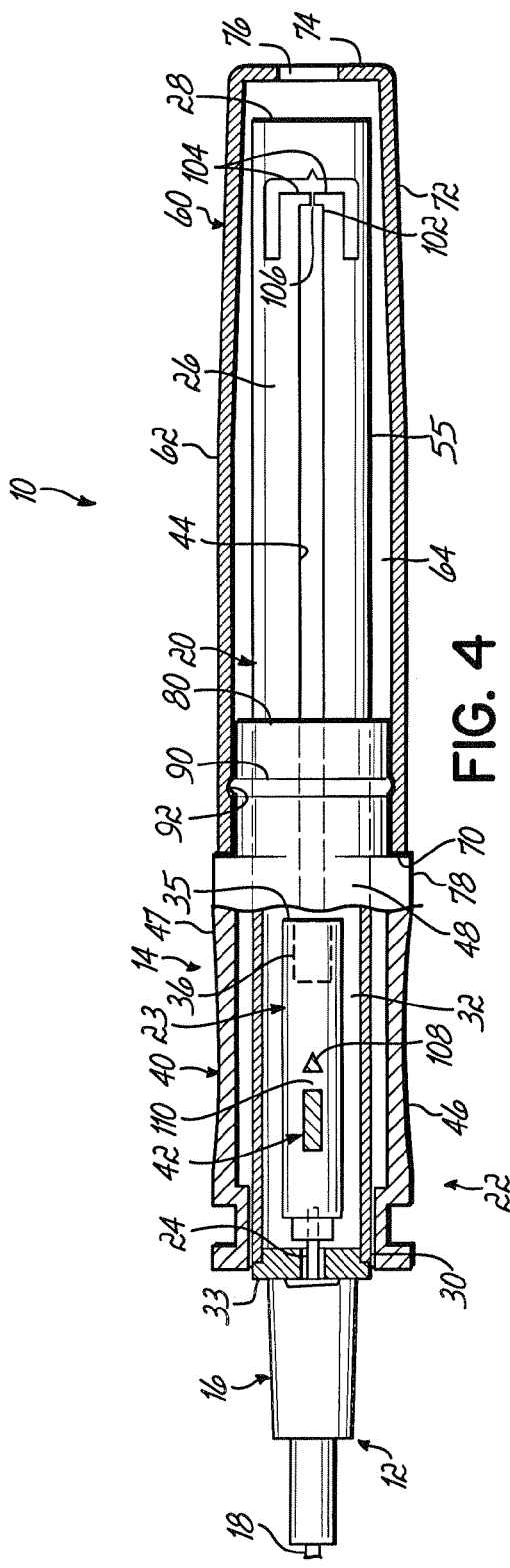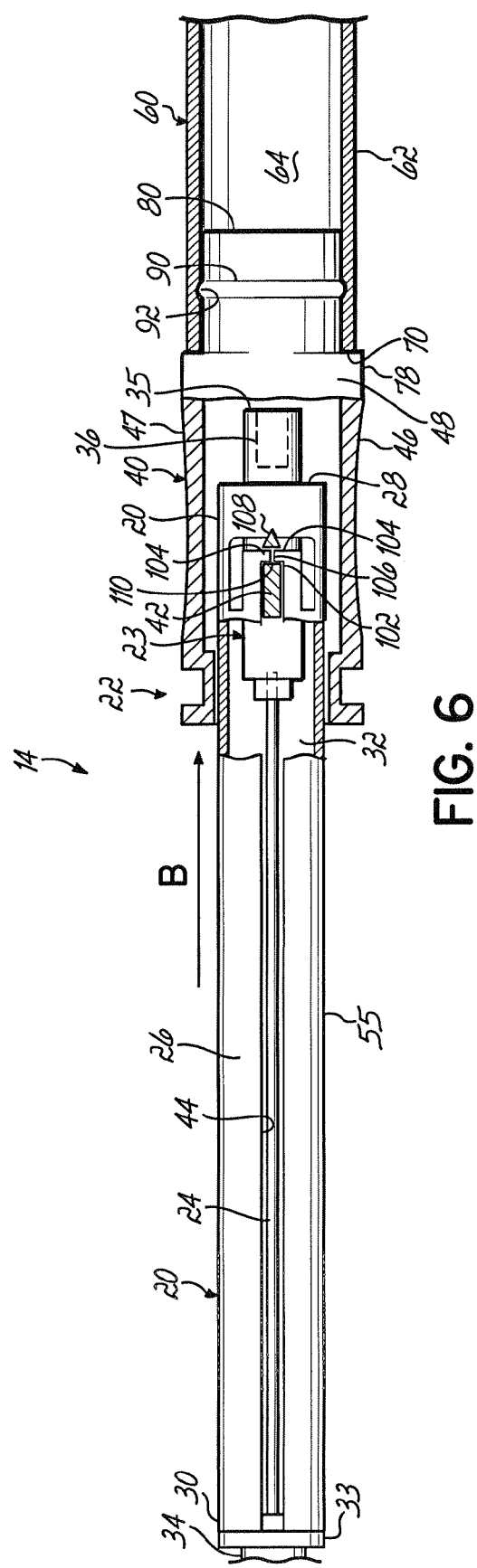

ENCLOSED NEEDLE CANNULA DEVICE WITH PROXIMAL END CAP

FIELD OF THE INVENTION

The present invention relates to enclosed needle devices.

DESCRIPTION OF PRIOR ART

Over-the-needle catheters are well known in the art. In such devices, a needle cannula projects through a catheter tube with its sharp tip projecting out of the distal end of the tube. The sharp tip of the needle cannula is used to pierce the skin and the blood vessel so as to carry the distal end of the catheter tube into the vessel. Once the catheter tube is in place, the needle cannula is withdrawn leaving the catheter hub exposed for use such as for connection to a medical fluid line or the like to administer or withdraw fluids.

In order to reduce the risks of accidental needle sticks after the needle cannula has been removed from the catheter, various proposals have been made to shield the needle tip. One class of devices intended to shield the needle tip includes an elongated needle guard housing into which the needle cannula is received as it is pulled proximally out from the catheter. The needle guard housing may include as part of its distal end a nose adapted to engage with the catheter hub and to be pulled free therefrom. The nose could be similar to a male slip luer that frictionally engages the female luer tapered interior surface of the catheter hub and/or could include structure by which to selectively release from the catheter hub, one example of which may be the duckbill release mechanism shown in U.S. patent application Ser. No. 11/276,152, filed Feb. 16, 2006. An important aspect of enclosed needle devices is that the needle guard housing is of sufficient length between its rear or proximal end and its front nose or distal end that it essentially encloses the entire length of the needle cannula therein when the needle cannula is pulled out of the catheter, thus shielding the needle tip. Advantageously, the sharp tip may extend into or be inside the nose to thus maintain alignment of the needle cannula, although, the sharp tip could instead be fully inside the needle guard housing. Either way, however, the needle cannula is considered to be enclosed, and the tip shielded. To that end, the needle cannula is supported on a needle support having an inner component movable within the needle guard housing from a first or ready position at which the distal end of the needle support is positioned toward the distal end of the needle guard housing with the needle cannula extending out of the nose of the needle guard housing (and through the catheter with the needle tip exposed when the needle guard housing is mounted to the catheter hub), to a second or shielded position with the distal end of the needle support positioned away from the distal end of the needle guard housing so as to withdraw the needle cannula to be enclosed by the needle guard housing. Advantageously, movement of the needle support in the second position is limited, and may be restricted by a locking mechanism. After moving into the second, shielded position, the needle guard housing may be removed from the catheter hub and discarded with the needle cannula shielded therein, leaving the catheter hub accessible as necessary.

Advantageously, the needle support is manually movable to the second position such as by manipulation of an exposed gripping component of the needle support. The exposed gripping component is positioned exteriorly of the needle guard housing, and attaches to the needle support component within the needle guard housing, such as via a rib(s) extending through a slot(s) in the needle guard housing. The exposed gripping component may be comprised of shaped surfaces defining wings disposed to opposites sides of the needle guard housing and designed to cooperate with the fingers of a user, and may include one or more further surfaces extending between and coupling the wing surfaces. The further surface (s) may be disposed above and/or below the needle guard housing. Where two such further surfaces are provided, the exposed gripping component effectively encircles the needle guard housing thereat. Each wing may be attached to the interior component of the needle support via a respective rib extending through slots on opposite sides of the needle guard housing, or a further surface of the gripping component may be attached to the interior component of the needle support via a rib extending through a single slot extending along the bottom or the top of the needle guard housing. An example of an enclosed needle device is the highly successful ProtectIV® Safety I.V. Catheter marketed by Smiths Medical ASD, Inc., the assignee hereof.

SUMMARY OF THE INVENTION

While enclosed needle devices that use an elongated needle guard housing to shield the needle tip by enclosing the needle cannula with a manually movable needle support have been well-accepted and are in widespread use, further improvement is desired. In that regard, the exposed gripping component of the needle support is generally and desirably much shorter than the length of the needle guard housing. As insertion and placement of the catheter into the patient generally occurs while the needle support is in or near the first position, a large extent of the needle guard housing proximal of the needle support wings is exposed during catheter insertion and placement. Some users may find that the palm or inside of the hand may bear against the exposed proximal portion of the needle guard housing and create unwanted or uncontrolled movement of the needle guard housing. It may have been considered to simply use an elongated gripping component that is long enough to cover the proximal portion of the needle guard housing even in the first position of the support housing. That arrangement, however, presents difficulties for manufacture and assembly, and so is not considered to be a practical solution.

The present invention provides a solution for covering the needle guard housing in the first position of the needle support, but without the drawback noted above. To that end, and in accordance with the principles of the present invention, the otherwise exposed proximal portion of the needle guard housing is enclosed by a separate end cap, which may be tubular, positioned over the proximal portion of the needle guard housing and affixed to the needle support such as to the inner component thereof and/or the exposed gripping component. To assemble the device, the needle guard housing and needle support may be assembled, and thereafter, the end cap placed over the proximal end of the needle guard housing and into confronting and abutting relationship with the proximal aspect of the needle support and secured thereto. The proximal aspect of the gripping component may include an extension which fits within the end cap and includes a rib to mate with a groove in the end cap. The extension may be semi-tubular which presents a gap within the end cap. The end cap may be provided with orienting structure adapted to fit in the gap to rotationally align the end cap and/or provide hoop strength to the gripping component proximal portion. The end cap and gripping component are affixed together, such as by a snap fit of the rib and groove and/or by adhesive or ultrasonic bonding, by way of examples. Alternatively or additionally, the inner component of the needle support and the end cap may be secured together, such as by adhesive. A stem extending between the end cap and the inner component of the needle support within the needle guard housing may couple the end cap to the inner component. The stem may be part of the end cap and extend distally from the proximal end thereof and/or the stem could be a proximal extension of the inner component of the needle support. By coupling a proximal end cap to the needle support and over the proximal aspect of the needle guard housing, the affect of a longer exposed gripping component is achieved, but with a practical arrangement that overcomes difficulties for manufacture and assembly.

By virtue of the foregoing, there is thus provided an enclosed needle device which has the advantages of the manually movable needle support, and has the effect of an elongated exposed gripping component, but without the drawbacks thereof. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate an exemplary embodiment of the invention and, together with a general description of the invention given above, and the detailed description given below, serve to explain the invention.

FIG. 2 is an exploded, perspective, partial view of the needle insertion assembly of the enclosed needle catheter insertion device of FIG. 1 for purposes of explaining the principles of the present invention;

FIG. 3 is a view taken along lines 3-3 of FIG. 1 with the needle guard housing removed for sake of clarity;

FIG. 3A is a view similar to FIG. 3 but showing an alternative version of end cap;

FIG. 4 is a partially cut-away, bottom view of a portion of the enclosed needle catheter insertion device of FIG. 1;

FIG. 6 is a partially cut-away, bottom view of a portion of the insertion needle assembly of FIG. 4 in the second or shielded position;

DETAILED DESCRIPTION OF THE DRAWINGS

With reference to FIGS. 1 through 6 (which are not necessarily to scale in order to show the various components more readily), there is shown a first exemplary embodiment 10 of a safety catheter device, also referred to as a catheter insertion device, having a catheter assembly 12 and needle insertion assembly 14 of the enclosed needle type with features of the present invention.

Figure 1:
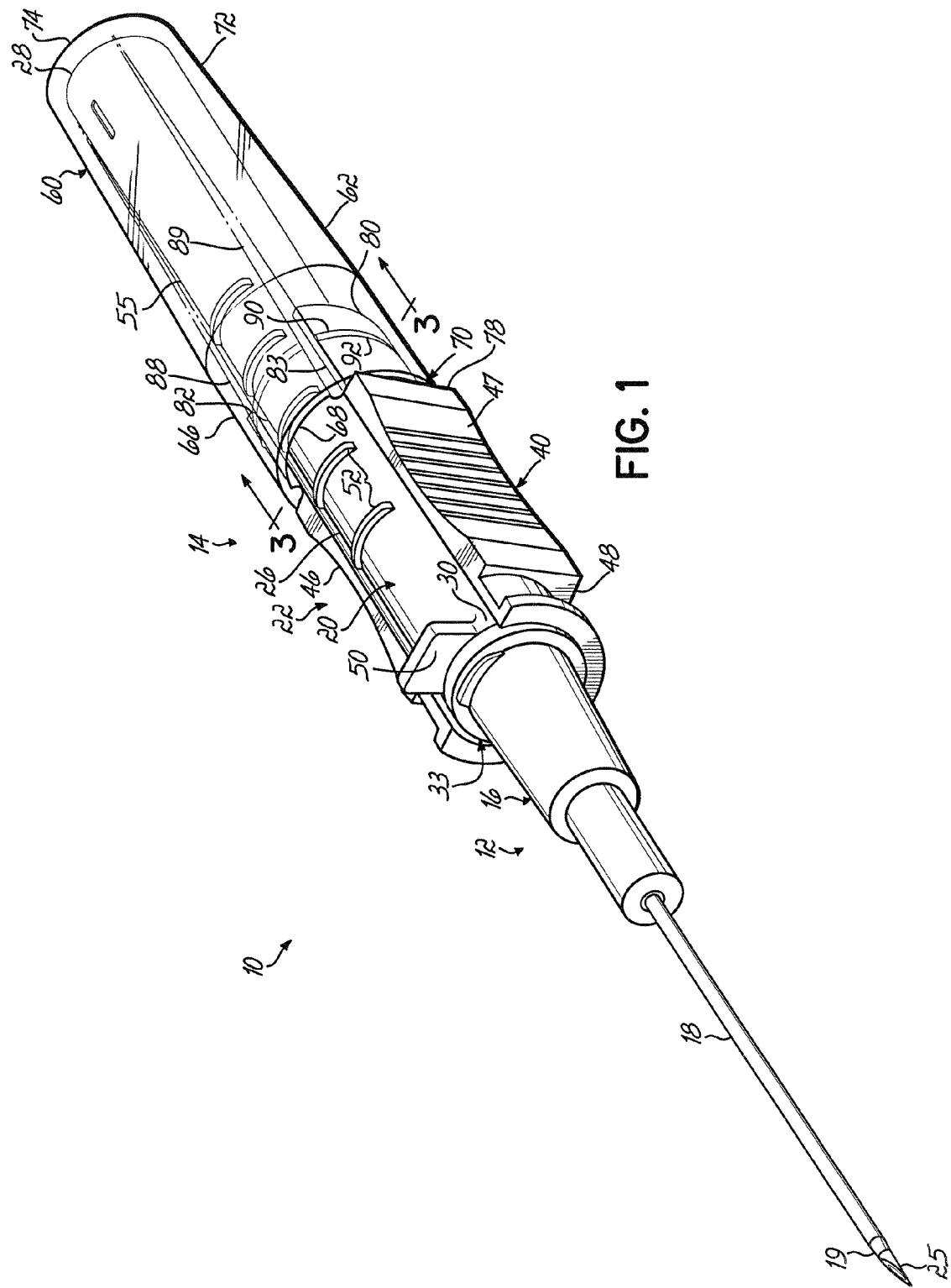
FIG. 1 is a perspective view of a first embodiment of an enclosed needle catheter insertion device in a first or ready position including a catheter assembly and a needle insertion assembly of the enclosed needle type with one version of an end cap in accordance with the principles of the present invention.

Catheter assembly 12 includes a catheter hub 16 and a catheter tube 18 extending distally therefrom to its distal, advantageously beveled, end 19. Needle insertion assembly 14 includes an elongated, advantageously cylindrical, needle guard housing 20, a needle support 22 including an elongated, advantageously cylindrical, inner component 23 (FIGS. 4 and 6) telescopingly received in guard housing 20, and a needle cannula 24 affixed to and extending distally from needle support 22 to a sharp, beveled tip 25 (FIG. 1). Needle guard housing 20 has a sidewall 26 extending between proximal end 28 and distal end 30 and defines therewithin a space 32 (FIGS. 4 and 6) through which the inner component 23 of needle support 22 moves and into which needle cannula 24 is ultimately received as will be described below. Mounted to distal end 30 of guard housing 20 and thus considered part of guard housing 20 is a cap 33 including a distally projecting nose 34 adapted to mate with catheter hub 16. Nose 34 may include a formed-in-place gasket (not shown) as described in U.S. Pat. No. 5,092,845 and/or may include one or more co-molded seals (also not shown) as described in co-pending U.S. patent application Ser. No. 11/276,155. Inner component 23 of needle support 22 is advantageously hollow so as to receive blood therein from needle cannula 24 to provide flashback. The proximal end 35 of inner component 23 of needle support 22 is advantageously closed off with a flash plug 36 of venting material which can pass air but not blood or other fluids.

Needle support 22 also includes an exposed gripping component 40 disposed exteriorly of needle guard housing 20 and which may advantageously be generally semi-tubular. Gripping component 40 is coupled to needle inner component 23 via a rib 42 extending through longitudinal slot 44 in sidewall 26 of needle guard housing 20. Gripping component 40 advantageously includes at least one sidewall or surface 46 or 47 shaped as a wing disposed to one side of needle guard housing 20, and shaped to facilitate manipulation with the fingers of a user (not shown). Advantageously gripping component 40 includes both sidewalls or surfaces 46 and 47 disposed to opposite sides of needle guard housing 20. In the embodiment shown in FIGS. 1 through 6, gripping component 40 also includes lower further surface 48 extending between and connecting wings 46, 47 below needle guard housing 20 and confronting slot 44 to thus define a semi-tubular shape to gripping component 40 about sidewall 26 of needle guard housing 20 in the area of wings 46, 47. Surface 48 may be flat or curved as desired. Distal end 30 of needle guard housing 20 may include a push or finger tab 50, and needle guard housing 20 may include arcuate ribs 52 spaced along sidewall 26. The bevel of sharp tip 25 of needle cannula 24 may be advantageously aligned with tab 50 as shown herein.

Needle insertion assembly 14 has a first or ready position as seen in FIGS. 1, 2, and 4 in which needle support 22 is positioned adjacent distal end 30, such that needle cannula 24 extends substantially beyond end 30 and cap 33, thereby exposing sharp tip 25. When catheter assembly 12 is mounted to needle insertion assembly 14, tip 25 is exposed beyond end 19 of catheter tube 18 in the ready position. It will be appreciated that in the first or ready position, a substantial portion 55 (such as approximately one-half or more of the axial length) of needle guard housing 20 proximal of gripping component 40 would be exposed behind gripping component 40 such that the palm or inside of a user's hand (not shown) might impact thereagainst during use of device 10. To that end, and in accordance with the principles of the present invention, needle insertion assembly 14 is provided with a proximal end cap 60 which is a separate component from at least gripping component 40 if not the entirety of needle support 22, but is positioned over proximal portion 55 of needle guard housing 20 and affixed to needle support 22 as explained below.

Proximal end cap 60 has a sidewall 62 defining an interior space 64 adapted to receive therein portion 55 of needle guard housing 20 which would otherwise be exposed proximal of gripping component 40 in the first or ready position. Sidewall 62 may advantageously define a tubular shape to proximal end cap 60. As seen particularly in FIG. 2, proximal end cap 60 may have a first or distal cylindrical aspect 66 supporting an open mouth 68 at the distal-most end 70 of cap 60 for receiving needle guard housing 20 therethrough and for mating with gripping component 40 as will be described. Cap 60 may have a second or proximal aspect 72 which tapers slightly to a proximal end wall 74 extending radially inwardly sufficient to be within the cylinder of needle guard housing 20 to effectively close off the proximal aspect 72. Wall 74 may include an aperture 76 therein for venting of the space 64 (and thus of needle insertion assembly 14).

With needle support 22 and gripping component 40 assembled to needle guard housing 20, proximal end cap 60 is mounted over proximal end 28 of needle guard housing 20 through mouth 68 in the direction of Arrow A in FIG. 2 until end 70 of cap 60 is confronting and abutting proximal end 78 of gripping component 40. Cap 60 and component 40 are affixed thereat. In the embodiment shown in the Figures, proximal end 78 of gripping component 40 includes a proximal extension 80 such as a semi-tubular segment sized to fit snugly within mouth 68 of cap 60. Segment 80 has edges 82, 83 to define a gap 84 therebetween. End cap 60 includes orienting structure 85 presenting surfaces 86, 87 to confront and generally abut edges 82, 83 within gap 84 so as to rotationally align end cap 60 with gripping component 40 and/or provide hoop strength to proximal extension 80 thereof. As seen in FIGS. 2 and 3, orienting structure 85 could be defined by rails 88, 89 extending proximally from adjacent mouth 68 on sidewall 62 to define respective surfaces 86, 87. Alternatively, as seen in FIG. 3A, orienting structure 85 could be a solid, arcuate thickened portion 62a of sidewall 62 extending proximally from adjacent mouth 68 to define respective surfaces 86, 87. Further, segment 80 may include a circumferential or arcuate rib 90 thereabout, and cap 60 may include an recess or groove 92 sized to receive rib 90 therein in a snap fit arrangement by which to affix cap 60 to gripping component 40. Groove 92 could extend circumferentially or along an arc between rails 88 and 89 or could be annular and extend completely in circle. Alternatively or additionally, cap 60 and gripping component 40 may be attached together with adhesive and/or ultrasonic bonding.

Figure 5:
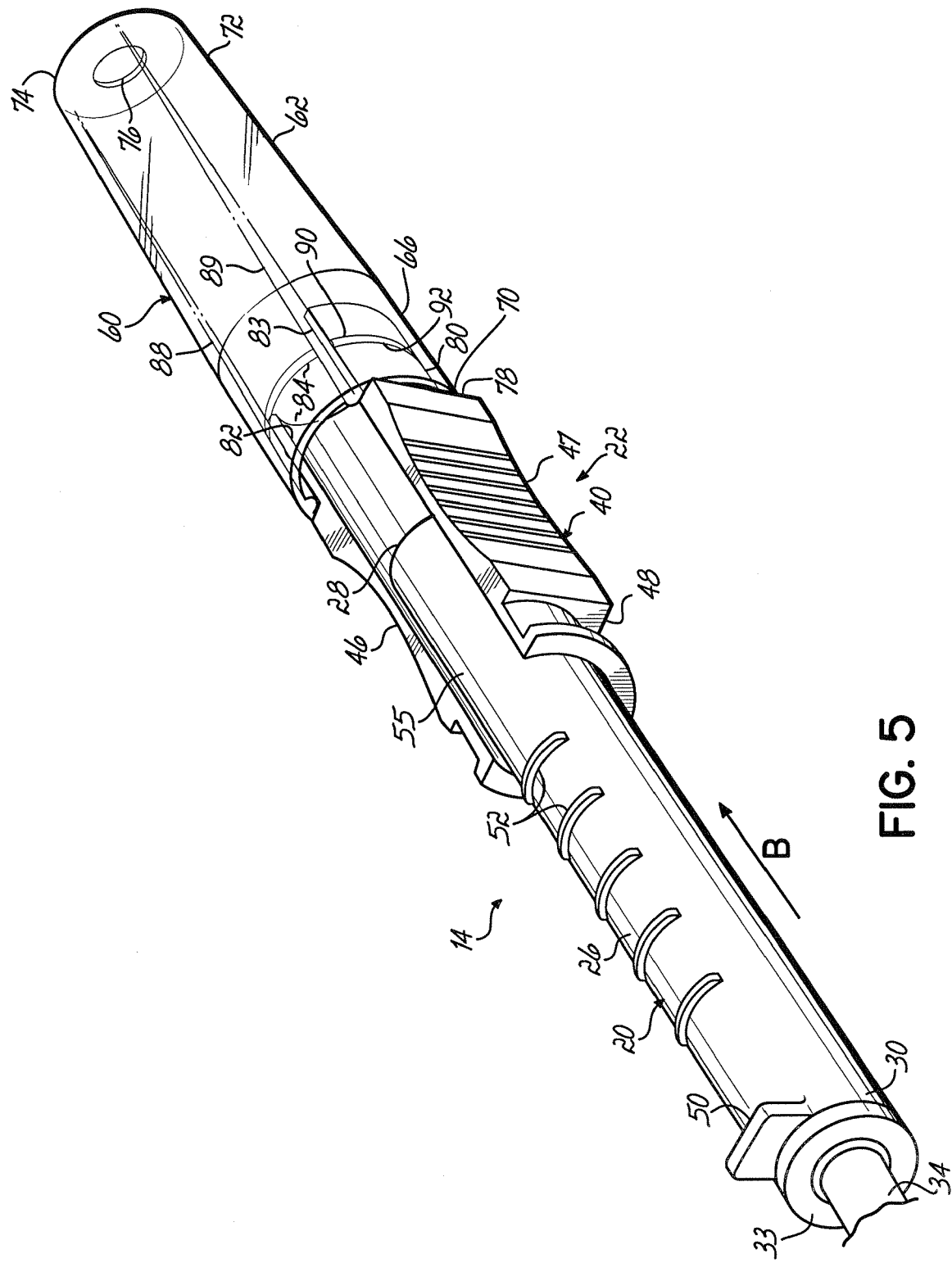
FIG. 5 is a perspective view of a portion of the insertion needle assembly of FIG. 1 in a second or shielded position with the catheter assembly removed for purposes of explaining the principles of the present invention.
Figure 7:
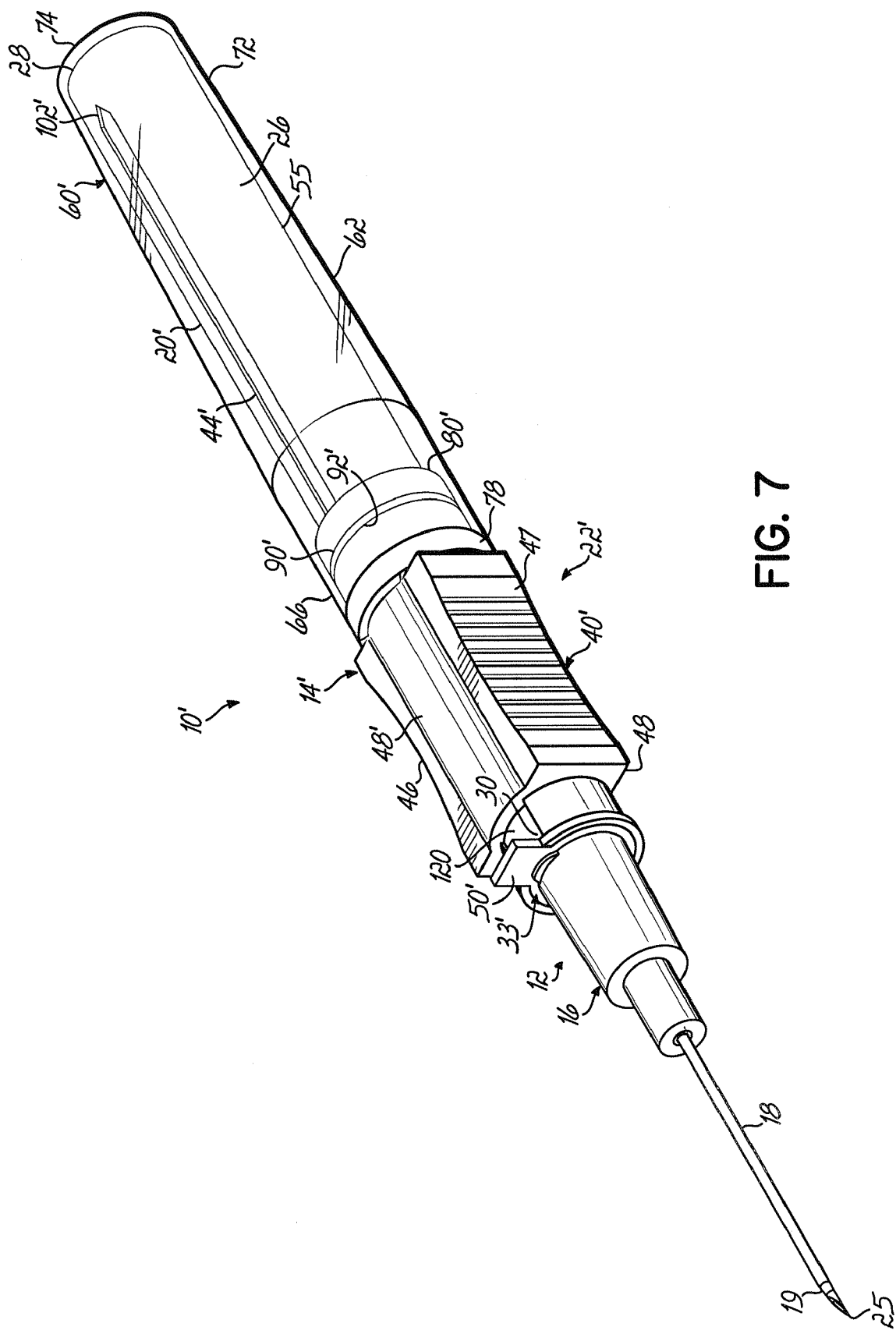
FIG. 7 is a perspective view of a second embodiment of an enclosed needle catheter insertion device in a first or ready position including a catheter assembly and a needle insertion assembly of the enclosed needle type with a further version of end cap in accordance with the principles of the present invention.
Figure 8:
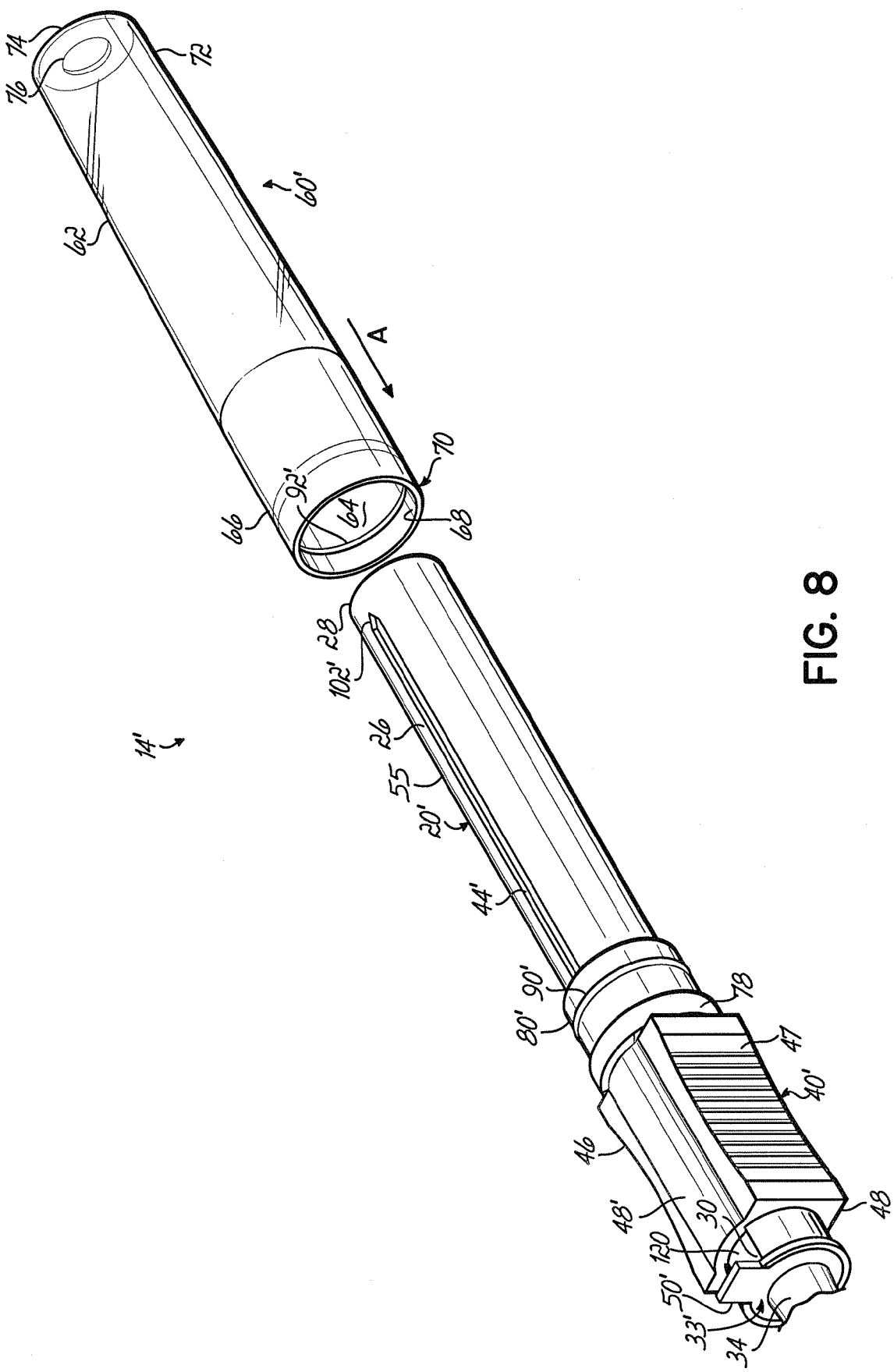
FIG. 8 is an exploded, perspective, partial view of the needle insertion assembly of the enclosed needle catheter insertion device of FIG. 7 for purposes of explaining the principles of the present invention.
Figures 9, 11:
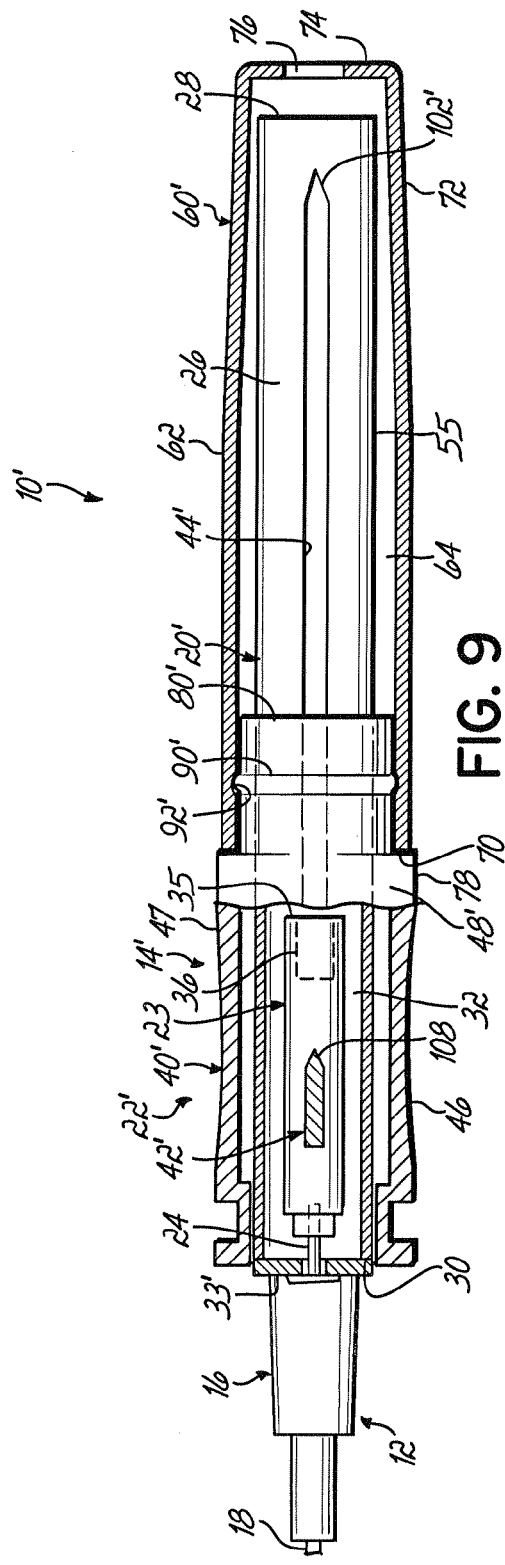
FIG. 9 is a partially cut-away, top view of a portion of the enclosed needle catheter insertion device of FIG. 7.
FIG. 11 is a partially cut-away, top view of a portion of the insertion needle assembly of FIG. 7 in the second or shielded position.
Figure 10:
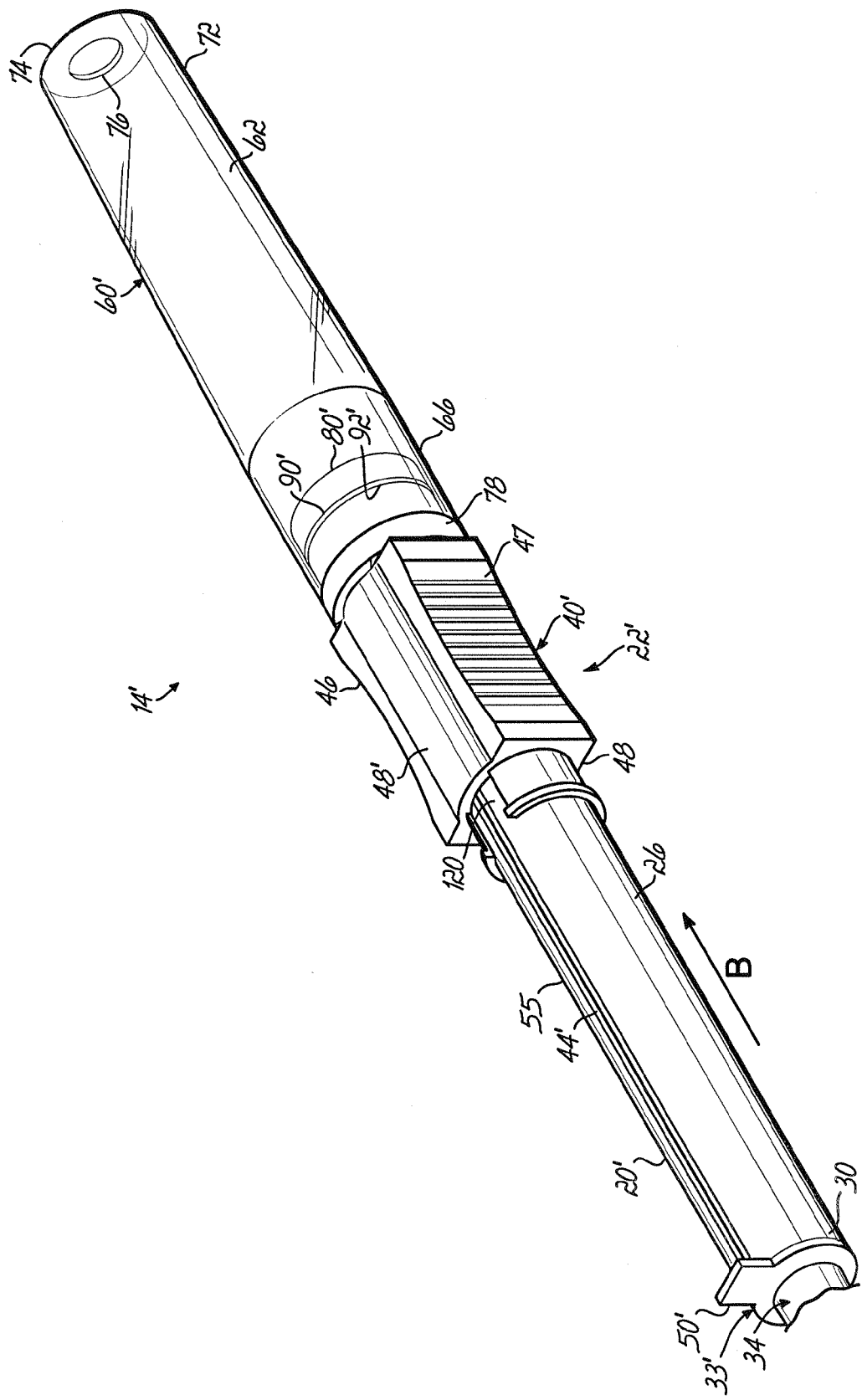
FIG. 10 is a perspective view of a portion of the insertion needle assembly of FIG. 7 in a second or shielded position with the catheter assembly removed for purposes of explaining the principles of the present invention.

Needle insertion assembly 14 has a second position seen in FIGS. 5 and 6 in which needle cannula 24 is shielded within needle guard housing 20. The second position is achieved by manually manipulating gripping component 40 to pull it proximally in the direction of Arrow B in FIGS. 5 and 6 so as to pull needle support 22 away from the distal end 30 of needle guard housing 20 until it is adjacent proximal end 28 thereof. That manipulation brings needle tip 25 into at least nose 34 if not into space 32 so as to enclose or shield needle cannula 24. Needle insertion assembly 14 may optionally include a locking mechanism to hold needle support 22 in the second position. To that end, and with reference to FIGS. 4 and 6, the proximal end 102 of slot 44 is provided a U-shape so as to include a pair of fingers 104, the fingers defining a slot 106 therebetween. Fingers 104 are each adapted to cam or be urged away from each other to widen slot 106 for a proximally tapered aspect 108 of rib 42 to pass therebetween. As aspect 108 of rib 42 passes completely beyond fingers 104, slot 106 closes back down into gap area 110 defined in rib 42 distal of aspect 108 to prevent fingers 104 from moving out of that position. Although defined as part of rib 42, aspect 108 could also be a separate rib spaced apart from rib 42 by gap area 110.

The needle insertion assembly 14 is easily assembled by affixing needle cannula 24 to needle support 22, and then inserting needle support 22 (and flash plug 36) into needle guard housing 20 by passing rib 42 (and aspect 108) into slot 44 at distal end 30 such that gripping component 40 is external of needle guard housing 20. In that regard, slot 44 may be open or unblocked at end 30 for assembly purposes, and thereafter cap 33 is affixed to end 30 to also close or block slot 44 such that needle support 22 is retained for movement within needle guard housing by manipulation of gripping component 40 external of needle guard housing 20. Proximal end cap 60 is thereafter placed over the proximal end 28 of needle guard housing 20 as along Arrow A in FIG. 2, and is affixed to needle support 22 which, in the embodiment of FIGS. 1 through 6, is achieved by affixing end cap 60 to segment 80 of gripping component 40.

In use, needle support 22 will be in the first or ready position with proximal portion 55 of needle guard housing 20 enclosed by proximal end cap 60 such as to be generally shielded from unwanted or undesired interaction with the palm or inside of a user's hand (not shown). Any protective sheath (not shown) is removed, and needle cannula 24 may then be used to guide catheter tube 18 into a patient (not shown) and positioned as desired without the user's palm or inside of the hand adversely causing undesired or unnecessary movement of needle guard housing 20. Needle cannula 24 may then be moved to the second position as shown in FIGS. 5 and 6 by manual manipulation to move gripping component 40 proximally (along Arrow B in FIGS. 5 and 6) whereat needle cannula 24 is enclosed or shielded by needle guard housing 20 (in the embodiment shown herein, tip 25 extends into, and is within, nose 34 of guard housing 20, which is still defined as the needle cannula 24 being enclosed or shielded by needle guard housing 20). Needle insertion assembly 14 is removed from catheter hub 16. Needle assembly 14 may then be discarded, leaving catheter assembly 12 in place in the patient for vascular access purposes.

With further reference to FIGS. 7 through 11 (which are not necessarily to scale in order to show the various components more readily), there is shown a second embodiment 10' of a safety catheter or catheter insertion device similar to the embodiment 10 shown in FIGS. 1 through 6 with the same reference numbers being used for like components. To that end, device 10' also has catheter assembly 12 and has a needle insertion assembly 14' of the enclosed needle type with features of the present invention. Needle insertion assembly 14' is very much like needle insertion assembly 14 described hereinabove except as follows. (A) Needle guard housing 20' does not have the ribs (52) on sidewall 26 nor the finger tab (50) at its distal end 30. Instead, cap 33' closes off distal end 30 and includes thereon a push or finger tab 50'. (B) Gripping component 40' has sidewalls 46, 47 and lower further surface 48, but also includes a further upper surface 48' (which may be flat or curved as desired) extending between and connecting wings 46, 47 above needle guard housing 20', such that gripping component 40' is generally tubular so as to be generally closed about its periphery to thus encircle sidewall 26 of needle guard housing 20' in the area of wings 46, 47. (C) Slot 44' is on the top, rather than the bottom (in the case of slot 44), of needle guard housing 20', and rib 42' extends between upper surface 48' and inner component 23 of needle support 22'. (D) Slot 44' and rib 42' do not include a locking mechanism (although they optionally could). The proximal end 102' of slot 44' may simply be formed to match to tapered aspect 108 of rib 42', and need not include the fingers (104) or slot (106) of slot 44, nor does rib 42' require the gap area (110) of rib 42. Movement of the needle support 22' once in the second position in the embodiment of FIGS. 7-11 may be limited by a clip, tab, or other reorienting structure (not shown) associated with nose 34 that blocks tip 25 of needle cannula 24 after tip 25 has entered into nose 34, some examples of which are shown in U.S. Pat. Nos. 5,419,766, 5,683,365 and 6,322,537. (E) Gripping component 40' defines a notch 120 within which tab 50' of cap 33' fits in the first or ready position. (F) Proximal segment or extension 80' of gripping component 40' is generally tubular and so does not have a gap (84), such that proximal end cap 60', which may otherwise be identical to proximal end cap 60, advantageously does not include orienting structure (85) to rotationally align end cap 60' with gripping component 40'. And, (G) rib 92' of segment 80' is annular and extends completely around segment 80' and/or provide hoop strength to proximal extension 80'. Assembly and use of device 10' is substantially the same as that described above in connection with device 10.

Figure 12:
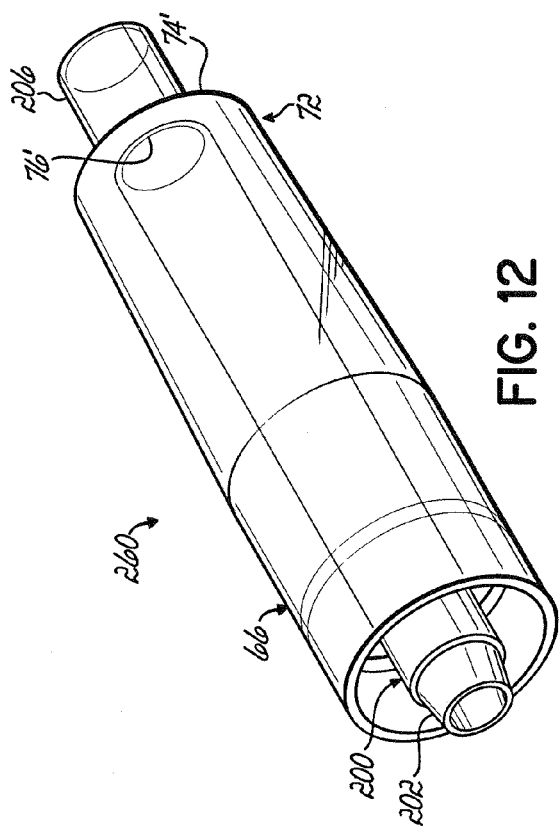
FIG. 12 is a perspective view of a further version of an end cap in accordance with the principles of the present invention.
Figure 13:
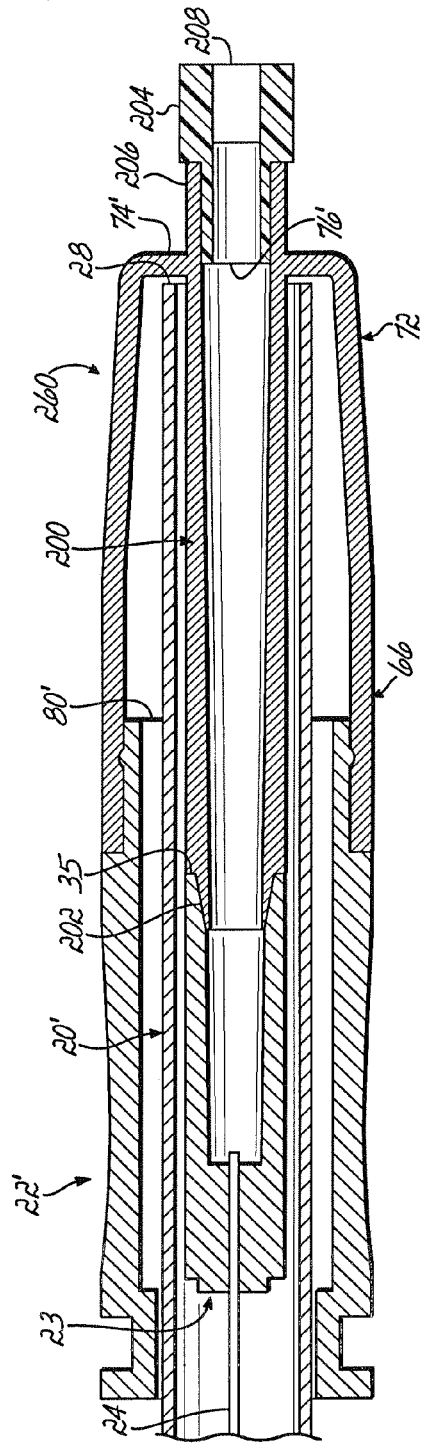
FIG. 13 is a cross-sectional view of the end cap of FIG. 12 affixed to the needle support of FIG. 7 for purposes of explaining the principles of the present invention.

In the foregoing embodiments, the end cap (60 or 60') has been affixed to the proximal extension (80 or 80') of the gripping component (40 or 40') in order to affix to the needle support 22 or 22'. Additionally, or alternatively, the end cap could be affixed to the needle support by coupling to the proximal end 35 thereof. To that end, and with reference to FIGS. 12 and 13, a stem 200 may be coupled between the inner component 23 of needle support 22' and end cap 260 (which could otherwise be substantially the same as end cap 60 or 60'). Stem 200 may be securely affixed to proximal end 35 of needle support 22' and to proximal aspect 72, such as proximal end wall 74', of end cap 260. Stem 200 in the embodiment shown in FIGS. 12 and 13 is hollow and is formed integrally with end cap 260 to extend distally from end wall 74' to a free, distal end 202. Stem end 202 attaches to proximal end 35 so as to define an effective extension of inner component 23 to, or out of, proximal end 28 of needle guard housing 20' even in the first position. In that regard, inner component 23 would not need to be provided with a flash plug 36. Instead, distal end 202 of stem 200 is shaped to snugly fit into proximal end 35 of inner component 23 in fluid tight arrangement therewith so as to effectively extend the flashback chamber and achieve the affect shown in co-pending U.S. patent application Ser. No. 11/276,154. Ends 202 and 35 could further be adhesively bonded or otherwise secured together. A flash plug 204 is removably received in port 206 extending proximally from end wall 74', with port 206 fluidicly coupled to aperture 76' in end cap 260. Flash plug 204 includes material 208 like flash plug material 36 as described in relation to devices 10 and 10' above. Flash plug 204 normally stays in place against passage of fluids through inner component 23, but plug 204 can be removed, giving the medical practitioner (not shown) fluid communication access into and through component 23 and needle cannula 24 as desired.

While stem 200 is shown as being an integral portion of end cap 260, some or all of stem 200 could be provided by a proximal extension of inner component 23 of needle support 22' as will be readily appreciated. Further, while end cap 260 is also shown as having cylindrical aspect 66 affixed to proximal extension 80' as described above in connection with end cap 60' (or could be affixed to extension 80 of needle support 22 and may also include orienting structure 85), end cap 260 need not include all of cylindrical aspect 66 (or orienting structure 85 if used with needle support 22) such that there could be a gap (not shown) between end cap 260 and exposed gripping component 40'. Assembly is substantially as above-described in connection with devices 10 and 10' except that the affixation would involve or include coupling of stem 200 between end cap 260 and needle support component 23, as above-described. Use of such devices with end cap 260 would be substantially as described above for devices 10 and 10'.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. For example, gripping component 40 or 40' may be attached to needle support 22 or 22' by more than rib 42 or 42' (and/or its tapered aspect 108). In that regard, neither of surfaces 48 or 48' need be provided and/or each of wings 46, 47 may couple to needle support 22 or 22' via a separate rib extending through a respective slot 44 or 44' of needle guard housing 20 or 20'. Also, while it is advantageous to have proximal end wall 74 for end cap 60 or 60' such that they have an aspect within the cylinder of needle guard housing 20', proximal end cap 60 or 60' need not have vent aperture 76 and/or proximal end wall 74. Further, end caps 60, 60' or 260 need not necessarily enclose all of portion 55 of needle guard housing 20 or 20'. The invention in its broader aspects is therefore not limited to the specific details, representative apparatus and method, and illustrated examples shown and described. Accordingly, departures may be made from such details without departing from the scope or spirit of Applicant's general inventive concept.

Having described the invention what is claimed is:

1. An enclosed needle device comprising:
   an elongated needle guard housing having a proximal end and a distal end;
   a needle support having an inner component movable within the needle guard housing between a first position adjacent the distal end of the needle guard housing and a second position adjacent the proximal end of the needle guard housing;
   a needle cannula affixed to and extending distally from the needle support for movement therewith and terminating in a sharp distal tip, the sharp tip of the needle being exposed out beyond the distal end of the needle guard housing in the first position of the needle support and the needle cannula being enclosed within the needle guard housing in the second position of the needle support;
   the needle support having an exposed gripping component external of the needle guard housing and attached to the needle support inner component within the needle guard housing such that manual manipulation of the gripping component results in movement of the needle support inner component, the gripping component being adjacent the distal end of the needle guard housing in the first position of the needle support and being sized to expose a substantial portion of the needle guard housing proximal of the gripping component in the first position of the needle support; and a proximal end cap external of the needle guard housing and being separate from and affixed to the needle support, the end cap being sized to receive therein and substantially enclose the portion of the needle guard housing proximal of the gripping component in the first position of the needle support.

2. The enclosed needle device of claim 1, the needle guard housing including a distal nose portion.

3. The enclosed needle device of claim 1, the gripping component including a wing to one side of the needle guard housing.

4. The enclosed needle device of claim 3, the gripping component further including a second wing to an opposite side of the needle guard housing.

5. The enclosed needle device of claim 4, the gripping component further including a surface below the needle guard housing interconnecting the wings.

6. The enclosed needle device of claim 5, the gripping component further including a second surface above the needle guard housing interconnecting the wings.

7. The enclosed needle device of claim 1, the gripping component defining a generally tubular structure.

8. The enclosed needle device of claim 1, the gripping component being generally closed about its periphery.

9. The enclosed needle device of claim 1, the gripping component having a proximal end, the end cap having a distal end affixed to the gripping component proximal end.

10. The enclosed needle device of claim 1, the gripping component having a proximal extension received within the end cap.

11. The enclosed needle device of claim 10, the proximal extension having a gap, the end cap including orienting structure receivable in the gap.

12. The enclosed needle device of claim 11, the end cap being affixed to the inner component of the needle support.

13. The enclosed needle device of claim 12, further comprising a stem coupled between the inner component of the needle support and the end cap.

14. The enclosed needle device of claim 1, the end cap being generally tubular.

15. The enclosed needle device of claim 14, the end cap having a proximal wall closing off the proximal end of the end cap.

16. The enclosed needle device of claim 15, the proximal wall of the end cap having an aperture therethrough.

17. The enclosed needle device of claim 1, the end cap having a proximal wall closing off the proximal end of the end cap.

18. The enclosed needle device of claim 17, the proximal wall of the end cap having an aperture therethrough.

19. The enclosed needle device of claim 1, the needle guard housing having a longitudinal slot, the enclosed needle device further comprising a rib extending through the slot attaching the gripping component to the needle support.

20. A safety catheter device comprising:
a catheter assembly including a catheter hub and a catheter tube extending distally from the catheter hub distal end; and an enclosed needle device coupled to the catheter assembly comprising:
an elongated needle guard housing having a proximal end and a distal end;
a needle support having an inner component movable within the needle guard housing between a first position adjacent the distal end of the needle guard housing and a second position adjacent the proximal end of the needle guard housing;
a needle cannula affixed and extending distally from the needle support for movement therewith and terminating in a sharp distal tip, the sharp tip of the needle being exposed out beyond the distal end of the needle guard housing and the catheter tube in the first position of the needle support and the needle cannula being enclosed within the needle guard housing in the second position of the needle support;
the needle support having an exposed gripping component external of the needle guard housing and attached to the needle support inner component within the needle guard housing such that manual manipulation of the gripping component results in movement of the needle support inner component, the gripping component being adjacent the distal end of the needle guard housing in the first position of the needle support and being sized to expose a substantial portion of the needle guard housing proximal of the gripping component in the first position of the needle support; and
a proximal end cap external of the needle guard housing and being separate from and affixed to the needle support, the end cap being sized to receive therein and substantially enclose the portion of the needle guard housing proximal of the gripping component in the first position of the needle support.

21. The safety catheter device of claim 20, the needle guard housing including a distal nose portion.

22. The safety catheter device of claim 20, the gripping component including a wing to one side of the needle guard housing.

23. The safety catheter device of claim 22, the gripping component further including a second wing to an opposite side of the needle guard housing.

24. The safety catheter device of claim 23, the gripping component further including a surface below the needle guard housing interconnecting the wings.

25. The safety catheter device of claim 24, the gripping component further including a second surface above the needle guard housing interconnecting the wings.

26. The enclosed needle device of claim 20, the gripping component defining a generally tubular structure.

27. The safety catheter device of claim 20, the gripping component being generally closed about its periphery.

28. The safety catheter device of claim 20, the gripping component having a proximal end, the end cap having a distal end affixed to the gripping component proximal end.

29. The safety catheter device of claim 20, the gripping component having a proximal extension received within the end cap.

30. The safety catheter of claim 29, the proximal extension having a gap, the end cap including orienting structure receivable in the gap.

31. The enclosed needle device of claim 20, the end cap being affixed to the inner component of the needle support.

32. The enclosed needle device of claim 21, further comprising a stem coupled between the inner component of the needle support and the end cap.

33. The safety catheter device of claim 20, the end cap being generally tubular.

34. The safety catheter device of claim 33, the end cap having a proximal wall closing off the proximal end of the end cap.

35. The safety catheter device of claim 34, the proximal wall of the end cap having an aperture therethrough.

36. The safety catheter device of claim 20, the end cap having a proximal wall closing off the proximal end of the end cap.

37. The safety catheter device of claim 36, the proximal wall of the end cap having an aperture therethrough.

38. The safety catheter device of claim 20, the needle guard housing having a longitudinal slot, the enclosed needle device further composing a rib extending through the slot attaching the gripping component to the needle support housing.

39. A method of assembling an enclosed needle guard comprising:

assembling a needle support with a needle extending therefrom for movement within a needle guard housing between a first position adjacent a distal end of the needle guard housing with a sharp distal tip of the needle being exposed out beyond the distal end of the needle guard housing and a second position adjacent the proximal end of the needle guard housing with the needle being enclosed within the needle guard housing, and a gripping component external of the needle guard housing for moving the needle support within the needle guard housing; and placing an end cap over a proximal end of the needle guard housing into confronting and abutting relationship with the needle support, and affixing the end cap and the needle support.

40. The method of claim 39 further comprising affixing the end cap and the needle support by affixing the end cap and an inner component of the needle support extending with the needle guard housing.

41. The method of claim 40 further comprising affixing the end cap and the needle support by affixing the end cap and the gripping component.

42. The method of claim 39 further comprising affixing the end cap and the needle support by affixing the end cap and the gripping component.

* * * * *

UNITED STATES PATENT AND TRADEMARK OFFICE
CERTIFICATE OF CORRECTION

PATENT NO. : 7,736,342 B2
APPLICATION NO. : 11/755200
DATED : June 15, 2010
INVENTOR(S) : Oscar R. Abriles and Thomas T. Koehler It is certified that error appears in the above-identified patent and that said Letters Patent is hereby corrected as shown below:

Column 2
Lines 3-4, "surface (s)" should be -- surface(s) --

Claim 38
Column 11, line 15, "further composing" should be -- further comprising --

Signed and Sealed this

Second Day of November, 2010

David J. Kappos
*Director of the United States Patent and Trademark Office*